US009788549B2

United States Patent
Wood

(10) Patent No.: US 9,788,549 B2
(45) Date of Patent: Oct. 17, 2017

(54) BROAD SPECTRUM DISINFECTANT

(71) Applicant: DISINFECTION RESEARCH LLC, La Jolla, CA (US)

(72) Inventor: Peter Wood, La Jolla, CA (US)

(73) Assignee: SPECTRUM DOXYICIDE, LLC, Denver, CO (US)

( * ) Notice: Subject to any disclaimer, the term of this patent is extended or adjusted under 35 U.S.C. 154(b) by 24 days.

(21) Appl. No.: 14/631,806

(22) Filed: Feb. 25, 2015

(65) Prior Publication Data

US 2015/0237864 A1 Aug. 27, 2015

Related U.S. Application Data

(60) Provisional application No. 61/945,054, filed on Feb. 26, 2014.

(51) Int. Cl.
*A01N 59/00* (2006.01)

(52) U.S. Cl.
CPC .................................... *A01N 59/00* (2013.01)

(58) Field of Classification Search
None
See application file for complete search history.

(56) References Cited

U.S. PATENT DOCUMENTS

| 4,731,193 A | 3/1988 | Mason et al. |
| 5,165,910 A | 11/1992 | Oikawa et al. |
| 2004/0166136 A1 | 8/2004 | Morelli et al. |
| 2005/0008554 A1 | 1/2005 | Nowosielski-Slepowron et al. |
| 2011/0000860 A1 | 1/2011 | Bland et al. |

FOREIGN PATENT DOCUMENTS

| CN | 1275324 A | 12/2000 |
| CN | 102626104 A | 8/2012 |
| EP | 2452565 A1 | 5/2012 |

OTHER PUBLICATIONS

Who, Concise International Chemical Assessment Document 37 for Chlorine Dioxide, 2002.*
Application Bulletin Deionized Water 2012 [downloaded on Jan. 7, 2016 from the website http://www.myronl.com/PDF/application_bulletins/di_ab.pdf].*
International Search Report and Written Opinion in PCT Application No. PCT/US2015/017605 dated Jun. 19, 2015.

* cited by examiner

*Primary Examiner* — Robert A Wax
*Assistant Examiner* — Thor Nielsen
(74) *Attorney, Agent, or Firm* — Michael R Shevlin

(57) ABSTRACT

Disclosed are devices, systems, and methods for producing broad spectrum disinfectants using a colloidal suspension of chlorine dioxide in deionized water, and more particularly, producing chlorine dioxide compositions that clean, disinfect and/or sterilize in one step with no harmful byproducts.

32 Claims, No Drawings

BROAD SPECTRUM DISINFECTANT

CROSS-REFERENCE TO RELATED APPLICATIONS

This application claims priority to U.S. Provisional Application No. 61/945,054, filed Feb. 26, 2014, which is incorporated herein by reference.

FIELD

The present invention is generally related to broad spectrum disinfectants using chlorine dioxide compositions, and more particularly, to methods for producing chlorine dioxide compositions that clean, disinfect and/or sterilize in one step with no harmful byproducts.

BACKGROUND

A hospital-acquired infection, also known as a HAI or in medical literature as a nosocomial infection, is an infection whose development is favored by a hospital environment, such as one acquired by a patient during a hospital visit or one developing among hospital staff. Such infections include fungal and bacterial infections and are aggravated by the reduced resistance of individual patients. [See "Nosocomial Infection". A Dictionary of Nursing. Oxford Reference Online. 2008].

In the United States, the Centers for Disease Control and Prevention estimated roughly 1.7 million hospital-associated infections, from all types of microorganisms, including bacteria, combined, cause or contribute to 99,000 deaths each year. Nosocomial infections can cause severe pneumonia and infections of the urinary tract, bloodstream and other parts of the body. Many types are difficult to attack with antibiotics, and antibiotic resistance is spreading to Gram-negative bacteria that can infect people outside the hospital. [See Pollack, Andrew. "Rising Threat of Infections Unfazed by Antibiotics" New York Times, Feb. 27, 2010]. In March 2009, the CDC released a report estimating overall annual direct medical costs of healthcare-associated infections ranged from $28-45 billion. [See Scott R D. The direct medical costs of healthcare-associated infections in US hospitals and the benefits of prevention, 2008. CDC].

CRE, which stands for Carbapenem-Resistant Enterobacteriaceae, are a family of germs that are difficult to treat because they have high levels of resistance to antibiotics. *Klebsiella* species and *Escherichia coli* (*E. coli*) are examples of Enterobacteriaceae, a normal part of the human gut bacteria that can become carbapenem-resistant. Types of CRE are sometimes known as KPC (*Klebsiella Pneumoniae Carbapenemase*) and NDM (New Delhi Metallo-beta-lactamase). KPC and NDM are enzymes that break down carbapenems and make them ineffective.

Healthy people usually do not get CRE infections. In healthcare settings, CRE infections most commonly occur among patients who are receiving treatment for other conditions. Patients whose care requires devices like ventilators (breathing machines), urinary (bladder) catheters, or intravenous (vein) catheters, and patients who are taking long courses of certain antibiotics are most at risk for CRE infections. Some CRE bacteria have become resistant to most available antibiotics. Infections with these germs are very difficult to treat, and can be deadly—one report cites they can contribute to death in up to 50% of patients who become infected. [See "CDC: Action needed now to halt spread of deadly bacteria: Data show more inpatients suffering infections from bacteria resistant to all or nearly all antibiotics" (Press release). The Centers for Disease Control. Mar. 5, 2013].

Hospitals have sanitation protocols regarding uniforms, equipment sterilization, washing, and other preventive measures. Thorough hand washing and/or use of alcohol rubs by all medical personnel before and after each patient contact is one of the most effective ways to combat nosocomial infections. Despite sanitation protocol, patients cannot be entirely isolated from infectious agents. Furthermore, patients are often prescribed antibiotics and other antimicrobial drugs to help treat illness; this may increase the selection pressure for the emergence of resistant strains. [See McBryde E S, Bradley L C, Whitby M, McElwain D L (October 2004). "An investigation of contact transmission of methicillin-resistant *Staphylococcus aureus*". J. Hosp. Infect. 58 (2): 104-8].

Sanitizing surfaces is an often overlooked, yet crucial, component of breaking the cycle of infection in health care environments. Modern sanitizing methods such as NAV-CO2 have been effective against gastroenteritis, MRSA, and influenza agents. Use of hydrogen peroxide vapor has been clinically proven to reduce infection rates and risk of acquisition. Hydrogen peroxide is effective against endospore-forming bacteria, such as *Clostridium difficile*, where alcohol has been shown to be ineffective. Ultraviolet cleaning devices may also be used to disinfect the rooms of patients infected with *Clostridium difficile* after discharge.

Micro-organisms are known to survive on inanimate 'touch' surfaces for extended periods of time. This can be especially troublesome in hospital environments where patients with immunodeficiencies are at enhanced risk for contracting nosocomial infections. Touch surfaces commonly found in hospital rooms, such as bed rails, call buttons, touch plates, chairs, door handles, light switches, grab rails, intravenous poles, dispensers (alcohol gel, paper towel, soap), dressing trolleys, and counter and table tops are known to be contaminated with *Staphylococcus*, MRSA (one of the most virulent strains of antibiotic-resistant bacteria) and Vancomycin-Resistant *Enterococcus* (VRE). Objects in closest proximity to patients have the highest levels of MRSA and VRE. This is why touch surfaces in hospital rooms can serve as sources, or reservoirs, for the spread of bacteria from the hands of healthcare workers and visitors to patients. [See Wilks, S. A., Michels, H., Keevil, C. W., 2005, The Survival of *Escherichia Coli* O157 on a Range of Metal Surfaces, International Journal of Food Microbiology, Vol. 105, pp. 445-454; and U.S. Department of Defense-funded clinical trials, as presented at the Interscience Conference on Antimicrobial Agents and Chemotherapy (ICAAC) in Washington, D.C., Oct. 28, 2008].

When a patient is being treated in hospital with antibiotics, one side-effect is the increase in *Clostridium difficile* (*C. difficile*). When the bacteria are in a colon in which normal gut flora has been destroyed (usually after a broad-spectrum antibiotic such as clindamycin has been used), the gut becomes overrun with *C. difficile*. People are most often nosocomially infected in hospitals, nursing homes, or other medical institutions, although infection outside medical settings is increasing. *C. difficile* infection is a growing problem in healthcare facilities. The rate of *C. difficile* acquisition is estimated to be 13% in patients with hospital stays of up to two weeks, and 50% with stays longer than four weeks. [See Clabots, C. R.; Johnson, S.; Olson, M. M.; Peterson, L. R.; Gerding, D. N. (September 1992). "Acquisition of *Clostridium difficile* by hospitalized patients: evidence for colonized new admissions as a source of infection". Journal of Infectious Diseases 166 (3): 561-7].

Chlorine dioxide has generated interest for control of microbiological growth. Unlike chlorine, chlorine dioxide remains a gas when dissolved in aqueous solutions and does not ionize to form weak acids. The biocidal activity of chlorine dioxide is believed to be due to its ability to penetrate bacterial cell walls and react with essential amino acids within the cell cytoplasm to disrupt cell metabolism. Unfortunately, chlorine dioxide in solution is unstable with an extremely short shelf life. Chlorine dioxide solutions must typically be generated at its point of use such as, for example, by a reaction between a metal chlorate or metal chlorite in aqueous solution and a liquid phase strong acid. However, the use of liquid phase strong acids poses handling issues and safety concerns.

In view of this, it would be desirable to develop a broad spectrum disinfectant that is safe, efficacious and fast, has no harmful byproducts, cleans and disinfects and/or sterilizes in one step, has a long shelf life, and does not cause and is not affected by pathogenic mutation.

SUMMARY

In one aspect, the invention is a method of making a chlorine dioxide disinfectant solution. The method includes adding a first amount of hydrochloric acid solution to a second amount of sodium chlorite; agitating the hydrochloric acid solution and sodium chlorite to mix the chemicals into a hydrochloric acid/sodium chlorite solution containing chlorine dioxide molecules; adding a third amount of one or more stabilizers to the hydrochloric acid/sodium chlorite solution; mixing the stabilizers and hydrochloric acid/sodium chlorite solution; and adding a fourth amount of deionized water.

In one aspect, a 100% L of chlorine dioxide disinfectant solution is produced using:
the first amount=1.0-10.0% L of hydrochloric acid solution;
the second amount=1.0-10.0% L of sodium chlorite;
the third amount=0.005-7.0% L of one or more stabilizers; and
the fourth amount=73.0-97.995% L of deionized water.

In another aspect, a 100% L of chlorine dioxide disinfectant solution is produced using:
the first amount=4.0-8.0% L of hydrochloric acid solution;
the second amount=4.0-8.0% L of sodium chlorite;
the third amount=0.005-0.60% L of hypochlorite and 0.005-6.0% L of surfactant; and
the fourth amount=77.40-91.99% L of deionized water.

In another aspect, a 100% L of chlorine dioxide disinfectant solution is produced using:
the first amount=4.0-8.0% L of hydrochloric acid solution;
the second amount=4.0-8.0% L of sodium chlorite;
the third amount=0.005-1.00% L of hypochlorite and 0.005-6.0% L of phosphate; and
the fourth amount=77.00-91.99% L of deionized water.

In another aspect, a 100% L of chlorine dioxide disinfectant solution is produced using:
the first amount=4.0-8.0% L of hydrochloric acid solution;
the second amount=4.0-8.0% L of sodium chlorite;
the third amount=0.005-0.60% L of hypochlorite and 0.005-6.0% L of phosphate; and
the fourth amount=77.40-91.99% L of deionized water.

In another aspect, a 100% L of chlorine dioxide disinfectant solution is produced using:
the first amount=4.0-8.0% L of hydrochloric acid solution;
the second amount=4.0-8.0% L of sodium chlorite;
the third amount=0.005-0.60% L of hypochlorite and 0.005-6.0% L of surfactant; and
the fourth amount=77.40-91.99% L of deionized water.

In some aspects, the one or more stabilizers form colloidal structures surrounding the chlorine dioxide molecules, the colloidal structures being suspended in the deionized water. The one or more stabilizers may include one or more hypochlorites, one or more surfactants or one or more phosphates.

DETAILED DESCRIPTION

Embodiments of the invention will now be described with reference to the figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

The present invention provides aqueous solution of chlorine dioxide ($ClO_2$) from various reactions. For example, from the reaction of: sodium chlorite ($NaClO_2$) and hydrochloric acid (HCl), shown in Formula (1); potassium chlorate ($KClO_3$) and oxalic acid ($H_2C_2O_4$), shown in Formula (2); chloric acid ($HCO_3$) and hydrochloric acid (HCl), shown in Formula (3); sodium chlorite ($NaClO_2$), hydrochloric acid (HCl) and sodium Hypochlorite (NaOCl), shown in Formula (4).

$$4HCL + 5NaClO_2 \rightarrow 4ClO_2 + 2H_2O + 5NaCl \quad (1)$$

$$2KClO_3 + 2H_2C_2O_4 \rightarrow K_2C_2O_4 + 2ClO_2 + 2CO_2 + 2H_2O \quad (2)$$

$$HClO_3 + HCl \rightarrow HClO_2 + HOCl \quad (3)$$

$$2NaClO_2 + 2HCl + NaOCl \rightarrow 2ClO_2 + 3NaCl + H_2O \quad (4)$$

Chlorine dioxide ($ClO_2$) decomposes in light, is temperature sensitive and it reacts with most organic compounds. Chlorine dioxide is a dissolved gas which means its ability to stay in solution is also affected by the sizes of exposed liquid surface areas and vapor spaces in containers. At atmospheric pressure and 20° C. the solubility in water is approximately 70 g/l.

The stability of chlorine dioxide in water is enhanced using two mechanisms, colloidal formations and buffering. The mechanism chosen depends on how the product is to be used. For disinfectants, a phosphate may be used, and in the proper amount forms a colloidal structure with the phosphate molecules surrounding the $ClO_2$ molecules. The durability of the colloid may be optimized by the colloidal wall design and the performance of the disinfectant may be enhanced with micelles. The mixture of the chemicals is important for shelf life. Tests revealed $ClO_2$ will remain stable for years if the solution has the proper amount of sodium polyphosphate.

Aqueous solutions of chlorine dioxide are prepared with pure reagents that are substantially free of undesirable contaminants. For stability, the chlorine dioxide is combined with one or more selected stabilizing compounds. The disclosed aqueous solutions of chlorine dioxide can maintain a stable concentration over many months or longer and minimize the deleterious effects of increased temperature and physical agitation, both in storage and in transport.

General Instructions

All bottles and cylinders shall be labeled with the chemicals that they contain. Each container shall be rinsed with deionized water and openings to the atmosphere shall be covered to avoid contamination. Always rinse any container with deionized water before reusing.

All processes and reactions are carried out at room temperature not exceeding (20° C.) unless otherwise specified.

The present invention may be used for various products, including, for example, a surface disinfectant. While the present application discloses embodiments for a surface disinfectant, it is contemplated that the same processes, methods and solutions may be used for the other products.

Basic Solutions

Below are examples of the Basic Solutions that may be used for the Broad Spectrum Disinfectant.
1. Hydrochloric acid solution (HCl).
2. Sodium chlorite ($NaClO_2$).
3. Stabilizers, such as:
   3i Hypochlorite (OCl—), such as Calcium hypochlorite ($Ca(OCl)_2$), Sodium hypochlorite (NaOCl), Lithium hypochlorite (LiOCl), Hypochlorous acid (HOCl). Other examples may include Barium hypochlorite ($Ba(OCl)_2$), Potassium hypochlorite (KOCl), Strontium hypochlorite, ($Sr(OCl)_2$), Beryllium hypochlorite ($Be(OCl)_2$), Magnesium hypochlorite ($Mg(OCl)_2$), Methyl hypochlorite ($CH_3ClO$), t-Butyl hypochlorite.
   3ii Surfactant (for example, DOWFAX 3B2).
   3iii Phosphate, such as: Sodium polyphosphate (($NaPO_3)_n$), Sodium metaphosphate, Sodium hexametaphosphate, Sodium tripolyphosphate, Sodium pyrophosphate, Sodium trimetaphosphate, Ammonium phosphate (($NH_4)_3PO_4$), Ammonium metaphosphate, Potassium phosphate ($K_3PO_4$), Potassium polyphosphate, Potassium pyrophosphate, Potassium metaphosphate, Lithium phosphate ($Li_3PO_4$), Lithium orthophosphate, Lithium polyphosphate, Cesium phosphate ($Cs_3PO_4$)
4 Deionized water ($H_2O$).

Chlorine Dioxide Composition Products Types

Table 1 below shows a range of Basic Solutions used for a Broad Spectrum Disinfectant.

TABLE 1

| | Basic Solutions (100% L) | | | |
|---|---|---|---|---|
| Product type | 1 | 2 | 3 | 4 |
| Disinfectant | 1.0-10.0% | 1.0-10.0% | 0.005-7.0% | 73.0-97.995% |

In a general embodiment of a Broad Spectrum Disinfectant, a 100% L of chlorine dioxide disinfectant solution is produced using the Basic Solutions as follows:

1. 1.0-10.0% L of Hydrochloric acid solution (HCl).
2. 1.0-10.0% L of Sodium chlorite ($NaClO_2$).
3. 0.005-7.0% L of one or more Stabilizers.
4. 73.0-97.995% L of Deionized water ($H_2O$).

Table 2 below shows some example ranges of Basic Solutions that may be used for different embodiments of a Broad Spectrum Disinfectant.

TABLE 2

| | Basic Solutions (100% L) | | | | | |
|---|---|---|---|---|---|---|
| Disinfectant | 1 | 2 | 3i | 3ii | 3iii | 4 |
| Embodiment 1 | 4-8% | 4-8% | 0.005-0.60% | 0.005-6.0% | 0 | 77.40-91.99% |
| Embodiment 2 | 4-8% | 4-8% | 0.005-1.00% | 0 | 0.005-6.0% | 77.00-91.99% |
| Embodiment 3 | 4-8% | 4-8% | 0.005-0.60% | 0 | 0.005-6.0% | 77.40-91.99% |
| Embodiment 4 | 4-8% | 4-8% | 0.005-0.60% | 0.005-6.0% | 0 | 77.40-91.99% |

In Embodiment 1 of a Broad Spectrum Disinfectant, a 100% L of chlorine dioxide disinfectant solution is produced using the Basic Solutions as follows:
1. 4.0-8.0% L of Hydrochloric acid solution (HCl).
2. 4.0-8.0% L of Sodium chlorite ($NaClO_2$).
3i. 0.005-0.60% L of Hypochlorite.
3ii. 0.005-6.0% L of Surfactant.
4. 77.40-91.99% L of Deionized water ($H_2O$).

In Embodiment 2 of a Broad Spectrum Disinfectant, a 100% L of chlorine dioxide disinfectant solution is produced using the Basic Solutions as follows:
1. 4.0-8.0% L of Hydrochloric acid solution (HCl).
2. 4.0-8.0% L of Sodium chlorite ($NaClO_2$).
3i. 0.005-1.00% L of Hypochlorite.
3iii. 0.005-6.0% L of Phosphate.
4. 77.00-91.99% L of Deionized water ($H_2O$).

In Embodiment 3 of a Broad Spectrum Disinfectant, a 100% L of chlorine dioxide disinfectant solution is produced using the Basic Solutions as follows:
1. 4.0-8.0% L of Hydrochloric acid solution (HCl).
2. 4.0-8.0% L of Sodium chlorite ($NaClO_2$).
3i. 0.005-0.60% L of Hypochlorite.
3iii. 0.005-6.0% L of Phosphate.
4. 77.40-91.99% L of Deionized water ($H_2O$).

In Embodiment 4 of a Broad Spectrum Disinfectant, a 100% L of chlorine dioxide disinfectant solution is produced using the Basic Solutions as follows:
1. 4.0-8.0% L of Hydrochloric acid solution (HCl).
2. 4.0-8.0% L of Sodium chlorite ($NaClO_2$).
3i. 0.005-0.60% L of Hypochlorite.
3ii. 0.05-6.0% L of Surfactant.
4. 77.40-91.99% L of Deionized water ($H_2O$).

Chlorine dioxide ($ClO_2$) decomposes in light, is temperature sensitive and it reacts with most organic compounds. Clean production facilities and handling procedures, and material purity are essential to avoid reactions with organic contaminants.

Production Process

The production of chlorine dioxide solutions may be performed batch-wise or in continuous mode. Batch production is normally carried out in a single pot process, wherein the different components are added to a reaction container under a protocol as described in exact detail below. For continuous production, a special continuous mode reactor is used.

Preferably, the entire production process for the solution would be conducted under clean room conditions, in order to minimize the possibility of contamination of the solution by environmental contaminants, such as airborne particles. All contact surfaces, including without limitation surfaces of production equipment, filling equipment and packaging, should be thoroughly cleaned of particles prior to use.

Process for Preparation of the Stock Solutions

Ranges for the amounts of the Basic Solutions 1, 2, 3 and 4 to be used for each embodiment are shown in Tables 1 & 2 above.

1. Prepare the mixing process by decontaminating the container with chlorine dioxide followed by a rinse with deionized water. If the container is used regularly, the container may be rinsed with only deionized water. Ensure the container is empty before starting.
2. Add the hydrochloric acid solution to the container followed immediately by the sodium chlorite. When the hydrochloric acid and sodium chlorite solutions have been added, the funnel is removed and replaced with a cap. The cap should fit loosely in order to allow release of the gas formed in the container. Manually agitate the reagents back and forth a few times to help achieve proper mixing of the chemicals. CAUTION: Moderate gas formation is caused when mixing the hydrochloric acid and sodium chlorite solutions.
3. After 10 minutes, remove the cap and add the stabilizer for the individual product type being produced, Basic Solution 3 (one or more of 3A, 3B or 3C). Move the container back and forth a few times in order to achieve proper mixing of the chemicals. The reaction time after addition of the stabilizer is 12-15 minutes. During this time the mixture should be agitated at least two additional times. The reaction time should not exceed 20 minutes. CAUTION: Moderate gas formation is caused when mixing the stabilizer into the solution.
4. Add deionized water (basic solution for) to the container. The water temperature should not exceed 20° C., and the correct amount of water should be weighed in. WARNING: Very heavy gas formation is caused when adding the deionized water.

Batch Process Preparation of Stock Solution for a Broad Spectrum Disinfectant

Below shows one embodiment of a batch process for preparing N liters of Stock Solution for Surface Disinfectant.

A. Add the desired percentage of hydrochloric acid solution, for example 1.0-10.0%, to the container followed immediately by the desired percentage of sodium chlorite, for example 1.0-10.0%. Agitate the reagents back and forth a few times to help achieve proper mixing of the chemicals.

B. After 10 minutes, add the desired percentage of stabilizers, for example 0.005-7.0%, to the container. Move the container back and forth a few times in order to achieve proper mixing of the chemicals. The reaction time after addition of the stabilizer is 12-15 minutes. During this time the mixture should be agitated at least two additional times. The reaction time should not exceed 20 minutes.

C. Add the desired percentage of deionized water, for example 73.0-97.995%, preferably with a resistivity >10.0 MΩcm, to the container near the container bottom using the funnel with the extension tube. The water temperature should not exceed 20° C.

Continuous Process Preparation of Stock Solution for a Broad Spectrum Disinfectant Below shows one embodiment of a continuous process for preparing chlorine dioxide Surface Disinfectant.

A. Turn on the water pump in the reactor unit and adjust the deionized water to the desired feed rate.

B. Turn on the chemical solutions feed pumps and set the feed rates to the desired percentage of hydrochloric acid, sodium chlorite, and stabilizers.

C. Assure proper mixing of the water and chemicals.

Dilution—Preparation of Finished Product

The Solutions are diluted with deionized water in order to form the finished product solution. The concentration of chlorine dioxide in the finished product solution may vary. In one embodiment, the desired concentration of chlorine dioxide in the finished product solution is 5000 parts per million.

Handling of Stock Solution and Finished Product

When the stock solution has been prepared, it should be considered perishable. The Stock solution should be stored in a closed container, protected from light, at a temperature between 6-10° C. A storage temperature of 8° C. is recommended.

The maximum shelf life of the Stock Solution when stored under the above conditions is estimated to be 5 days when stored in a glass container or 2 days when stored in a polyethylene container.

After filling of the solution into the consumer containers, the filled Consumer Containers should be stored as described above for the Stock solution.

In some embodiments, the disinfectant solution is impregnated onto a cloth, such as paper or a fabric, to form disinfectant wipes. In some embodiments, the disinfectant solution is used to make disinfectant sprays.

It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claims set forth herebelow not be construed as being order-specific unless such order specificity is expressly stated in the claim.

The invention claimed is:

1. A method of making a chlorine dioxide disinfectant solution consisting of:
    adding a first amount of hydrochloric acid solution to a second amount of sodium chlorite;
    agitating the hydrochloric acid solution and sodium chlorite to mix the chemicals into a hydrochloric acid/sodium chlorite solution containing chlorine dioxide molecules;
    adding a third amount of one or more stabilizers to the hydrochloric acid/sodium chlorite solution, wherein the one or more stabilizers are selected from the group consisting of one or more hypochlorites and one or more phosphates;
    mixing the stabilizers and hydrochloric acid/sodium chlorite solution; and
    adding a fourth amount of deionized water.

2. The method of claim 1, wherein an L of chlorine dioxide disinfectant solution is produced using the following amounts:

the first amount=1.0-10.0% L of hydrochloric acid solution;

the second amount=1.0-10.0% L of sodium chlorite;

the third amount=0.005-7.0% L of one or more stabilizers; and the fourth amount=73.0-97.9% L of deionized water.

3. The method of claim 1, wherein the one or more stabilizers form colloidal structures surrounding the chlorine dioxide molecules, the colloidal structures being suspended in the deionized water.

4. The method of claim 1, wherein the deionized water has a minimum resistivity of 10.0 MΩ cm.

5. The method of claim 1, wherein an L of chlorine dioxide disinfectant solution is produced using the following amounts:

the first amount=4.0-8.0% L of hydrochloric acid solution;

the second amount=4.0-8.0% L of sodium chlorite;

the third amount=0.005-1.00% L of hypochlorite and 0.005-6.0% L of phosphate; and the fourth amount=77.00-91.99% L of deionized water.

6. The method of claim 1, wherein an L of chlorine dioxide disinfectant solution is produced using the following amounts:

the first amount=4.0-8.0% L of hydrochloric acid solution;

the second amount=4.0-8.0% L of sodium chlorite;

the third amount=0.005-0.60% L of hypochlorite and 0.005-6.0% L of phosphate; and the fourth amount=77.40-91.99% L of deionized water.

7. The method of claim 1, wherein the phosphate is selected from the group consisting of sodium polyphosphate, sodium metaphosphate, sodium hexametaphosphate, sodium tripolyphosphate, sodium pyrophosphate, sodium trimetaphosphate, ammonium phosphate, ammonium metaphosphate, potassium phosphate, potassium polyphosphate, potassium pyrophosphate, potassium metaphosphate, lithium phosphate, lithium orthophosphate, lithium polyphosphate, and cesium phosphate.

8. The method of claim 1, wherein the one or more hypochlorites is selected from the group consisting of calcium hypochlorite, sodium hypochlorite, lithium hypochlorite and hypochlorous acid.

9. The method of claim 1, further comprising diluting the concentration of chlorine dioxide within the deionized water.

10. The method of claim 1, wherein the diluted amount of chlorine dioxide in a finished chlorine dioxide disinfectant solution is 5000 parts per million.

11. The method of claim 10, further comprising filling a container with the chlorine dioxide disinfectant solution and closing the container.

12. The method of claim 1, wherein the method of making a chlorine dioxide disinfectant solution is a batch process.

13. The method of claim 1, wherein the method of making a chlorine dioxide disinfectant solution is a continuous process.

14. A continuous process method of making a chlorine dioxide disinfectant solution consisting of:

flowing deionized water at a desired feed rate in a reactor unit and;

flowing hydrochloric acid, sodium chlorite, and one or more stabilizers at desired percentages and desired feed rates to mix with the deionized water, wherein the one or more stabilizers are selected from the group consisting of one or more hypochlorites and one or more phosphates; and diluting the deionized water and chemical solutions such that a finished chlorine dioxide disinfectant solution contains 5000 parts per million of chlorine dioxide.

15. The method of claim 14, wherein the one or more phosphates is selected from the group consisting of sodium polyphosphate, sodium metaphosphate, sodium hexametaphosphate, sodium tripolyphosphate, sodium pyrophosphate, sodium trimetaphosphate, ammonium phosphate, ammonium metaphosphate, potassium phosphate, potassium polyphosphate, potassium pyrophosphate, potassium metaphosphate, lithium phosphate, lithium orthophosphate, lithium polyphosphate, and cesium phosphate.

16. The method of claim 14, wherein the one or more hypochlorites is selected from the group consisting of calcium hypochlorite, sodium hypochlorite, lithium hypochlorite and hypochlorous acid.

17. The method of claim 14, further comprising filling a container with the chlorine dioxide disinfectant solution and closing the container.

18. A method of making a chlorine dioxide disinfectant solution comprising the following steps:

step A:
adding a first amount of hydrochloric acid solution to a second amount of sodium chlorite;

agitating the hydrochloric acid solution and sodium chlorite to mix the chemicals into a hydrochloric acid/sodium chlorite solution containing chlorine dioxide molecules;

step B:
after a first desired time period of at least 10 minutes adding a third amount of one or more stabilizers to the hydrochloric acid/sodium chlorite solution;

mixing the stabilizers and hydrochloric acid/sodium chlorite solution for a second desired time period of 12-15 minutes; and step C:
after adding a fourth amount of deionized water.

19. The method of claim 18, wherein an L of chlorine dioxide disinfectant solution is produced using the following amounts:

the first amount=1.0-10.0% L of hydrochloric acid solution;

the second amount=1.0-10.0% L of sodium chlorite;

the third amount=0.005-7.0% L of one or more stabilizers; and the fourth amount=73.0-97.9% L of deionized water.

20. The method of claim 18, wherein the one or more stabilizers form colloidal structures surrounding the chlorine dioxide molecules, the colloidal structures being suspended in the deionized water.

21. The method of claim 18, wherein the deionized water has a minimum resistivity of 10.0 MΩ cm.

22. The method of claim 18, wherein the one or more stabilizers are selected from the group consisting of one or more hypochlorites, one or more surfactants, and one or more phosphates.

23. The method of claim 22, wherein an L of chlorine dioxide disinfectant solution is produced using the following amounts:

the first amount=4.0-8.0% L of hydrochloric acid solution;

the second amount=4.0-8.0% L of sodium chlorite;

the third amount=0.005-0.60% L of hypochlorite and 0.005-6.0% L of surfactant; and the fourth amount=77.40-91.99% L of deionized water.

24. The method of claim 22, wherein an L of chlorine dioxide disinfectant solution is produced using the following amounts:
the first amount=4.0-8.0% L of hydrochloric acid solution;
the second amount=4.0-8.0% L of sodium chlorite;
the third amount=0.005-1.00% L of hypochlorite and 0.005-6.0% L of phosphate; and
the fourth amount=77.00-91.99% L of deionized water.

25. The method of claim 22, wherein an L of chlorine dioxide disinfectant solution is produced using the following amounts:
the first amount=4.0-8.0% L of hydrochloric acid solution;
the second amount=4.0-8.0% L of sodium chlorite;
the third amount=0.005-0.60% L of hypochlorite and 0.005-6.0% L of phosphate; and
the fourth amount=77.40-91.99% L of deionized water.

26. The method of claim 22, wherein an L of chlorine dioxide disinfectant solution is produced using the following amounts:
the first amount=4.0-8.0% L of hydrochloric acid solution;
the second amount=4.0-8.0% L of sodium chlorite;
the third amount=0.005-0.60% L of hypochlorite and 0.005-6.0% L of surfactant; and
the fourth amount=77.40-91.99% L of deionized water.

27. The method of claim 22, wherein the phosphate is selected from the group consisting of sodium polyphosphate, sodium metaphosphate, sodium hexametaphosphate, sodium tripolyphosphate, sodium pyrophosphate, sodium trimetaphosphate, ammonium phosphate, ammonium metaphosphate, potassium phosphate, potassium polyphosphate, potassium pyrophosphate, potassium metaphosphate, lithium phosphate, lithium orthophosphate, lithium polyphosphate, and cesium phosphate.

28. The method of claim 22, wherein the one or more hypochlorites is selected from the group consisting of calcium hypochlorite, sodium hypochlorite, lithium hypochlorite and hypochlorous acid.

29. The method of claim 18, further comprising diluting the concentration of chlorine dioxide within the deionized water.

30. The method of claim 18, wherein the diluted amount of chlorine dioxide in a finished chlorine dioxide disinfectant solution is 5000 parts per million.

31. The method of claim 30, further comprising filling a container with the chlorine dioxide disinfectant solution and closing the container.

32. The method of claim 18, wherein the method of making a chlorine dioxide disinfectant solution is a batch process.

* * * * *